United States Patent
Mysing et al.

(10) Patent No.: US 11,918,616 B1
(45) Date of Patent: Mar. 5, 2024

(54) BEVERAGE FOR EQUINES, OTHER HOOVED ANIMALS AND LIVESTOCK THAT ENCOURAGES THEM TO DRINK WATER AND METHOD OF PRODUCTION

(71) Applicants: Melissa Mysing, Covington, LA (US); Dawn Brown, Covington, LA (US)

(72) Inventors: Melissa Mysing, Covington, LA (US); Dawn Brown, Covington, LA (US)

( * ) Notice: Subject to any disclaimer, the term of this patent is extended or adjusted under 35 U.S.C. 154(b) by 0 days.

(21) Appl. No.: 18/157,647

(22) Filed: Jan. 20, 2023

Related U.S. Application Data

(60) Provisional application No. 63/423,914, filed on Nov. 9, 2022, provisional application No. 63/301,312, filed on Jan. 20, 2022.

(51) Int. Cl.
| | |
|---|---|
| *A61K 36/48* | (2006.01) |
| *A23K 10/30* | (2016.01) |
| *A23K 20/163* | (2016.01) |
| *A23K 20/20* | (2016.01) |
| *A23K 20/22* | (2016.01) |
| *A23K 20/24* | (2016.01) |
| *A23K 50/10* | (2016.01) |
| *A23K 50/20* | (2016.01) |
| *A23K 50/30* | (2016.01) |
| *A61K 9/00* | (2006.01) |

(52) U.S. Cl.
CPC ............. *A61K 36/48* (2013.01); *A23K 10/30* (2016.05); *A23K 20/163* (2016.05); *A23K 20/22* (2016.05); *A23K 20/24* (2016.05); *A23K 20/30* (2016.05); *A23K 50/10* (2016.05); *A23K 50/20* (2016.05); *A23K 50/30* (2016.05); *A61K 9/0095* (2013.01)

(58) Field of Classification Search
CPC ...... A61K 36/48; A61K 9/0095; A23K 10/30; A23K 20/163; A23K 20/22; A23K 20/24; A23K 20/30; A23K 50/10; A23K 50/20; A23K 50/30
See application file for complete search history.

(56) References Cited

U.S. PATENT DOCUMENTS

| 8,883,232 B2 | 11/2014 | Baginski |
| 2003/0157190 A1 | 8/2003 | Woods |
| 2009/0252827 A1 | 10/2009 | Baginski |
| 2010/0021430 A1 | 1/2010 | Baginski |
| 2017/0347685 A1 | 12/2017 | Pohlman |
| 2017/0347686 A1 | 12/2017 | Pohlman |

*Primary Examiner* — Trevor Love
(74) *Attorney, Agent, or Firm* — Garvey, Smith & Nehrbass, Patent Attorneys, L.L.C.; Julia M. FitzPatrick; Vanessa M. D'Souza

(57) ABSTRACT

A beverage for equines, livestock (e.g., pigs, sheep, cattle, goats), or other hooved animals that encourages the animals to drink, providing hydration and electrolytes. The beverage is a combination of desired flavoring, e.g., a dry or powdered blend of alfalfa leaf powder or alfalfa meal; a sweetener, e.g., sugar; and one or more desired electrolytes, that is added to a liquid, e.g., water. Other desired flavoring can be mint, alfalfa mint, apple, peppermint.

22 Claims, 4 Drawing Sheets

| Nutrients | Per 94g Serving |
|---|---|
| Calories (kcal) | 268.50 |
| Fat (g) | 0 |
| Saturated Fat (g) | 0 |
| Trans Fatty Acid (g) | 0 |
| Cholesterol (mg) | 0 |
| Carbohydrates (g) | 64.99 |
| Dietary Fiber (g) | 5.00 |
| Total Sugars (g) | 49.90 |
| Added Sugar (g) | 49.90 |
| Protein (g) | 5.00 |
| Vitamins | |
| Vitamin D (mcg) | 0 |
| Minerals | |
| Sodium (mg) | 4100.25 |
| Calcium (mg) | 382.15 |
| Iron (mg) | 9.00 |
| Potassium (mg) | 2975.40 |
| Magnesium (mg) | 82.00 |
| Zinc (mg) | 2.90 |
| Copper (mg) | 2.30 |
| Manganese (mg) | 2.45 |

| Nutrients | Per 94g Serving |
|---|---|
| Calories (kcal) | 268.50 |
| Fat (g) | 0 |
| Saturated Fat (g) | 0 |
| Trans Fatty Acid (g) | 0 |
| Cholesterol (mg) | 0 |
| Carbohydrates (g) | 64.99 |
| Dietary Fiber (g) | 5.00 |
| Total Sugars (g) | 49.90 |
| Added Sugar (g) | 49.90 |
| Protein (g) | 5.00 |
| Vitamins | |
| Vitamin D (mcg) | 0 |
| Minerals | |
| Sodium (mg) | 4100.25 |
| Calcium (mg) | 382.15 |
| Iron (mg) | 9.00 |
| Potassium (mg) | 2975.40 |
| Magnesium (mg) | 82.00 |
| Zinc (mg) | 2.90 |
| Copper (mg) | 2.30 |
| Manganese (mg) | 2.45 |

FIG. 1

INGREDIENTS: Cane Sugar, Proprietary Hydration Blend of (Alfalfa Leaf Powder, Sodium Chloride, Potassium Chloride, Calcium Citrate, Magnesium Citrate, Zinc Gluconate, Copper Gluconate, Manganese Citrate), Maltodextrin Serving Size: 94g

| Nutrient | Label Claim |
|---|---|
| Calcium | 132.00 mg |
| Copper | 2.30 mg |
| Magnesium | 82.00 mg |
| Manganese | 2.45 mg |
| Potassium | 2450.00 mg |
| Sodium | 10,250.00 mg |
| Zinc | 2.90 mg |

| Nutrients | Per 94g Serving |
|---|---|
| Calories (kcal) | 268.50 |
| Fat (g) | 0 |
| Saturated Fat (g) | 0 |
| Trans Fatty Acid (g) | 0 |
| Cholesterol (mg) | 0 |
| Carbohydrates (g) | 64.99 |
| Dietary Fiber (g) | 5.00 |
| Total Sugars (g) | 49.90 |
| Added Sugar (g) | 49.90 |
| Protein (g) | 5.00 |

FIG. 2

| NUTRIENTS | PER 84G SERVING |
|---|---|
| CALORIES (KCAL) | 238.50 |
| FAT (G) | 0 |
| SATURATED FAT (G) | 0 |
| TRANS FATTY ACID (G) | 0 |
| CHOLESTEROL (MG) | 0 |
| CARBOHYDRATES (G) | 58.99 |
| DIETARY FIBER (G) | 3.00 |
| TOTAL SUGARS (G) | 49.90 |
| PROTEIN (G) | 3.00 |

Ingredients: Cane Sugar, Alfalfa, Sodium Chloride, Potassium Chloride, Maltodextrin, Calcium Citrate, Magnesium Citrate, Zinc Gluconate, Copper Gluconate, Manganese Citrate

FIG. 3

Product Description: Premix for Alfalfa Water Blend 1 v3 — Values calculated per 100g of product

| | | | | |
|---|---|---|---|---|
| Protein | total protein | 0 | g | |
| Carbohydrates | Sugars | 0.566 | g | |
| | added sugars | 0.566 | g | |
| | total carbohydrates | 16.064 | g | |
| Fiber | total Fiber | 0 | g | |
| Lipids/Fat | Trans Fatty Acids | 0 | g | |
| | Saturated Fat | 0 | g | |
| | total Lipids/Fat | 0.011 | g | |
| | Cholesterol | 0 | mg | |
| Sodium | total Sodium | 21,691.503 | mg | |
| Moisture | Water | 1.388 | g | |
| Ash | Ash | 81.506 | g | |
| Proximates | other proximates | 1.031 | g | |
| Energy | Total | 64.355 | kcal | |
| Nutrients | Manganese | 12.895 | mg | |
| | Chloride | 44,394.265 | mg | |
| | Potassium | 12,894.737 | mg | |
| | Magnesium | 496.177 | mg | |
| | Calcium | 694.737 | mg | |
| | Zinc | 15.263 | mg | |
| | Copper | 12.105 | mg | |

BEVERAGE FOR EQUINES, OTHER HOOVED ANIMALS AND LIVESTOCK THAT ENCOURAGES THEM TO DRINK WATER AND METHOD OF PRODUCTION

CROSS-REFERENCE TO RELATED APPLICATIONS

Priority to and/or the benefit of U.S. Provisional Patent Application Ser. No. 63/301,312, filed on 20 Jan. 2022, and U.S. Provisional Patent Application Ser. No. 63/423,914, filed on 9 Nov. 2022, each of which is hereby incorporated herein by reference thereto, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a beverage for equines that promotes hydration and can provide electrolytes to equines. More particularly, the present invention relates to an improved beverage for equines that encourages them to drink water, while providing hydration and electrolytes. The improved beverage can be made by adding a dry or powdered supplement including sugar and alfalfa leaf powder and electrolytes to water. The beverage can also be provided to livestock (e.g., sheep, goats, pigs, cattle), and/or to other hooved animals if desired.

2. General Background of the Invention

Many horses are picky drinkers. While on the road during a competition, for example, horses may refuse to drink when the water tastes different from what they are accustomed to.

There is a need in the art for a horse hauling beverage that provides a real solution for horses on the road that are picky drinkers to promote drinking during travelling.

There is also a need in the art for a mare recovery beverage that promotes hydration for mares after foaling and while lactating.

There is also a need in the art for a horse post-surgery recovery beverage providing important hydration after surgeries.

There is also a need in the art for a horse heat stress beverage, providing a great tasting treat to serve on a hot summer's day and that can be served chilled.

There is also a need in the art for a medical and supplement beverage, providing an easy way to deliver medications and supplements.

There is also a need in the art for a horse healthy digestion beverage promoting good hydration, which is beneficial in maintaining a healthy digestive track.

There is also a need in the art for a beverage that is delicious to horses to promote drinking.

There is also a need in the art for a beverage that promotes horse hydration and encourages a horse to drink water.

There is also a need in the art for a beverage for horses that compete that can provide quicker recovery of muscles through good hydration before, during and after competitions.

There is also a need in the art for a post workout beverage for equines, e.g., horses, that provides faster turnaround and bounce back after hard workouts, lessons and/or competition prep.

There is also a need in the art for a dry or powdered blend of desired ingredients, e.g., including alfalfa, that can be added to water to provide one or more beverages as set forth above.

There is also a need in the art for a dry or powdered blend of desired ingredients, e.g., including alfalfa, that can be added to water to make one or more beverages as set forth above to provide to equines, e.g., horses, ponies, zebras, mules or donkeys.

There is also a need in the art for a dry or powdered blend of desired ingredients, e.g., including alfalfa, that can be added to water to make one or more beverages as set forth above to provide to livestock (e.g., sheep, goats, pigs, cattle), and/or to other hooved animals if desired.

There is also a need in the art for a dry or powdered blend of desired ingredients, e.g., including alfalfa, that can be added to water and readily dissolve in water to make one or more beverages as set forth above to provide to livestock (e.g., sheep, goats, pigs, cattle), and/or to other hooved animals if desired.

The following U.S. Patents and Patent Publications are incorporated herein by reference:

| PAT. NO. | TITLE | ISSUE DATE MM/DD/YYYY |
| --- | --- | --- |
| 8,883,232 | HORSE FEED AND TREATMENT METHODS | 11/11/2014 |
| 2003/0157190 | METHOD OF INCREASING FERTILITY AND ATHLETIC PERFORMANCE IN HORSES | 08/21/2003 |
| 2009/0252827 | HORSE FEED AND METHODS OF TREATING HORSES | 10/08/2009 |
| 2010/0021430 | HORSE FEED AND TREATMENT METHODS | 01/28/2010 |
| 2017/0347685 | HORSE SUPPLEMENT CARRIER AND FEEDING PRODUCT | 12/07/2017 |
| 2017/0347686 | DRIED SUPPLEMENT PRODUCT | 12/07/2017 |

BRIEF SUMMARY OF THE INVENTION

One or more preferred embodiments of the present invention is a concentrated beverage for equines, e.g., horses, ponies, mules, donkeys, or zebras that encourages them to drink the beverage and provides hydration and electrolytes.

One or more preferred embodiments of the present invention is a sport drink or beverage for equines, e.g., horses, ponies, mules, donkeys, or zebras that encourages them to drink the beverage and provides hydration and electrolytes.

One or more preferred embodiments of the present invention is a concentrated beverage for livestock, e.g., sheep, cattle, pigs, goats, that encourages them to drink the beverage and provides hydration and electrolytes.

One or more preferred embodiments of the present invention is a sport drink or beverage for livestock, e.g., sheep, cattle, pigs, goats, that encourages them to drink the beverage and provides hydration and electrolytes.

One or more preferred embodiments of the present invention is a concentrated beverage for hooved animals that encourages them to drink the beverage and provides hydration and electrolytes.

One or more preferred embodiments of the present invention is a sport drink or beverage for hooved animals that encourages them to drink the beverage and provides hydration and electrolytes.

One or more preferred embodiments of the present invention is a concentrated beverage for hooved animals, livestock and/or equines, that encourages them to drink the beverage and provides hydration and electrolytes.

One or more preferred embodiments of the present invention is a sport beverage for hooved animals, livestock and/or equines that encourages them to drink the beverage and provides hydration and electrolytes.

In a preferred embodiment of the present invention, a beverage comprises water, alfalfa (e.g., alfalfa leaf powder or alfalfa meal or other desired alfalfa-based flavoring), sugar, and optionally one or more desired electrolytes.

In a preferred embodiment of the present invention, a beverage comprises water, alfalfa (e.g., alfalfa leaf powder or alfalfa meal or other desired alfalfa-based flavoring), sugar, and one or more desired electrolytes.

In another preferred embodiment of the present invention, a beverage comprises the following dry ingredients added to about 1 to 3 gallons of water:
  a) about 15 to 30 grams of alfalfa, e.g., alfalfa powder; and
  b) about 15 to 50 grams of sugar, e.g., cane sugar.

In another preferred embodiment of the present invention, a beverage comprises the following dry ingredients added to about 1 to 3 gallons of water:
  a) about 20 to 30 grams of alfalfa, e.g., alfalfa powder; and
  b) about 20 to 30 grams of sugar, e.g., cane sugar.

In another preferred embodiment of the present invention, a beverage comprises the following dry ingredients added to about 1 to 4 gallons of water:
  a) about 10 to 30 grams of alfalfa, e.g., alfalfa powder; and
  b) about 10 to 30 grams of sugar, e.g., cane sugar.

In another preferred embodiment of the present invention, a beverage comprises the following dry ingredients added to about 1 to 4 gallons of water:
  a) about 10 to 30 grams of alfalfa, e.g., alfalfa powder; and
  b) about 10 to 50 grams of sugar, e.g., cane sugar.

In another preferred embodiment of the present invention, a beverage comprises the following dry ingredients added to about 1 to 3 gallons of water:
  a) about 15 to 30 grams of alfalfa, e.g., alfalfa powder; and
  b) about 20 to 50 grams of sugar, e.g., cane sugar.

In one or more preferred embodiments of the present invention, a beverage comprises the following dry ingredients added to about 1 to 3 gallons of water:
  a) about 20 to 30 grams of alfalfa, e.g., alfalfa powder;
  b) about 20 to 30 grams of sugar, such as cane sugar; and
  c) one or more desired electrolytes, e.g., as follows:
    (i) Calcium min: about 82 mg; calcium max: about 132 mg;
    (ii) salt min: about 9,850 mg; salt max: about 10,650 mg;
    (iii) Copper min: about 2.3 mg; max: about 5 mg;
    (iv) Zinc min: about 2.9 mg; max: about 6.5 mg;
    (v) Potassium min: about 2,450 mg; max: about 5,000 mg;
    (vi) Magnesium min: about 82 mg; max: about 200 mg; and/or
    (vii) Manganese min: about 2.45 mg; max: about 5.5 mg.

In one or more preferred embodiments, a beverage of the present invention comprises the following dry ingredients added to about 1 to 3 gallons of water:
  a) about 15 to 30 grams of alfalfa, e.g., alfalfa powder;
  b) about 20 to 50 grams of sugar, such as cane sugar; and
  c) one or more desired electrolytes, e.g., as follows:
    (i) Calcium min: about 82 mg; calcium max: about 132 mg;
    (ii) salt min: about 9,850 mg; salt max: about 10,650 mg;
    (iii) Copper min: about 2.3 mg; max: about 5 mg;
    (iv) Zinc min: about 2.9 mg; max: about 6.5 mg;
    (v) Potassium min: about 2,450 mg; max: about 5,000 mg;
    (vi) Magnesium min: about 82 mg; max: about 200 mg; and/or
    (vii) Manganese min» about 2.45 mg; max: about 5.5 mg.

In one or more preferred embodiments, a beverage of the present invention comprises the following dry ingredients added to about 2 gallons of water:
  a) about 25 grams of alfalfa, e.g., alfalfa powder;
  b) about 25 grams of cane sugar; and
  c) electrolytes, e.g., as follows:
    (i) Calcium min: about 82 mg; calcium max: about 132 mg;
    (ii) salt min: about 9,850 mg; salt max: about 10,650 mg;
    (iii) Copper min: about 2.3 mg;
    (iv) Zinc min: about 2.9 mg;
    (v) Potassium min: about 2,450 mg;
    (vi) Magnesium min: about 82 mg; and/or
    (vii) Manganese min: about 2.45 mg.

In another preferred embodiment, the following dry ingredients are added to about 2 gallons of water:
  a) about 15 grams of alfalfa, e.g., alfalfa powder;
  b) about 50 grams of cane sugar; and
  c) electrolytes, e.g., as follows:
    (i) Calcium min: about 82 mg; calcium max: about 132 mg;
    (ii) salt min: about 9,850 mg; salt max: about 10,650 mg;
    (iii) Copper min: about 2.3 mg;
    (iv) Zinc min: about 2.9 mg;
    (v) Potassium min: about 2,450 mg;
    (vi) Magnesium min: about 82 mg; and/or
    (vii) Manganese min: about 2.45 mg.

In one or more preferred embodiments of a beverage of the present invention, the following dry ingredients are added to about 1 to 3 gallons of water:
  a) about 20 to 30 grams of alfalfa, e.g., alfalfa powder;
  b) about 20 to 30 grams of cane sugar; and
  c) one or more electrolytes, e.g., as follows:
    (i) about 82 to 200 mg Calcium;
    (ii) about 9,000 to 20,000 salt min;
    (iii) about 2.3 to 5.00 Copper min;
    (iv) about 2.9 to 6.5 mg Zinc;
    (v) 2,450 to 5,000 mg Potassium;
    (vi) about 82 to 200 mg Magnesium;
    (vii) about 2.45 to 5.5 mg, Manganese; and/or
    (viii) another desired electrolyte.

In one or more preferred embodiments of a beverage of the present invention, the following dry ingredients are added to about 1 to 3 gallons of water:
 a) about 15 to 30 grams of alfalfa, e.g., alfalfa powder;
 b) about 20 to 50 grams of cane sugar; and
 c) one or more electrolytes, e.g., as follows:
  (i) about 82 to 200 mg Calcium;
  (ii) about 9,000 to 20,000 salt min;
  (iii) about 2.3 to 5.00 Copper min;
  (iv) about 2.9 to 6.5 mg Zinc;
  (v) about 2,450 to 5,000 mg Potassium;
  (vi) about 82 to 200 mg Magnesium;
  (vii) about 2.45 to 5.5 mg, Manganese; and/or
  (viii) another desired electrolyte.

In one or more preferred embodiments of a method of making a beverage of the present invention, the following dry ingredients are added to about 1 to 4 gallons of water at room temperature, e.g., about 20 to 27 degrees Celsius or about 68 to 80 degrees Fahrenheit, mixed, e.g., stirred, and served to an equine, or to livestock (e.g., pigs, sheep, goats, cattle), or to another type of hooved animal:
 a) about 10 to 30 grams of alfalfa, e.g., alfalfa powder;
 b) about 10 to 30 grams of sugar, e.g., cane sugar; and
 c) one or more desired electrolytes, e.g., as follows:
  (i) Calcium min: about 82 mg; calcium max: about 132 mg;
  (ii) salt min: about 9,850 mg; salt max: about 10,650 mg;
  (iii) Copper min: about 2.3 mg; max: about 5.00;
  (iv) Zinc min: about 2.9 mg; max: about 6.5 mg;
  (v) Potassium min: about 2,450 mg; max: about 5,000 mg;
  (vi) Magnesium min: about 82 mg; max: about 200 mg; and/or
  (vii) Manganese min: about 2.45 mg; max: about 5.5 mg.

In one or more preferred embodiments of a method of making a beverage of the present invention, the following dry ingredients are added to about 1 to 4 gallons of water at room temperature, e.g., about 20 to 27 degrees Celsius or about 68 to 80 degrees Fahrenheit, mixed, e.g., stirred, and served to an equine, or to livestock (e.g., pigs, sheep, goats, cattle), or to another type of hooved animal:
 a) about 10 to 30 grams of alfalfa, e.g., alfalfa powder;
 b) about 10 to 50 grams of sugar, e.g., cane sugar; and
 c) one or more desired electrolytes, e.g., as follows:
  (i) Calcium min: about 82 mg; calcium max: about 132 mg;
  (ii) salt min: about 9,850 mg; salt max: about 10,650 mg;
  (iii) Copper min: about 2.3 mg; max: about 5.00;
  (iv) Zinc min: about 2.9 mg; max: about 6.5 mg;
  (v) Potassium min: about 2,450 mg; max: about 5,000 mg;
  (vi) Magnesium min: about 82 mg; max: about 200 mg; and/or
  (vii) Manganese min: about 2.45 mg; max: about 5.5 mg.

In another preferred embodiment of the method of the present invention, the following dry ingredients are added to about 2 gallons of water at room temperature, e.g., about 20 to 27 degrees Celsius or about 68 to 80 degrees Fahrenheit, mixed, e.g., stirred, and served to an equine, or to livestock (e.g., pigs, sheep, goats, cattle), or to another type of hooved animal:
 a) about 25 grams of alfalfa, e.g., alfalfa powder;
 b) about 25 grams of cane sugar; and
 c) electrolytes, e.g., as follows:
  (i) Calcium min: about 82 mg; calcium max: about 132 mg;
  (ii) salt min: about 9,850 mg; salt max: about 10,650 mg;
  (iii) Copper min: about 2.3 mg;
  (iv) Zinc min: about 2.9 mg;
  (v) Potassium min: about 2,450 mg;
  (vi) Magnesium min: about 82 mg; and
  (vii) Manganese min: about 2.45 mg In another preferred embodiment of the method of the present invention, the following dry ingredients are added to about 2 gallons of water at room temperature, e.g., about 20 to 27 degrees Celsius or about 68 to 80 degrees Fahrenheit, mixed, e.g., stirred, and served to an equine, or to livestock (e.g., pigs, sheep, goats, cattle), or to another type of hooved animal:
 a) about 15 grams of alfalfa, e.g., alfalfa powder;
 b) about 50 grams of cane sugar; and
 c) electrolytes, e.g., as follows:
  (i) Calcium min: about 82 mg; calcium max: about 132 mg;
  (ii) salt min: about 9,850 mg; salt max: about 10,650 mg;
  (iii) Copper min: about 2.3 mg;
  (iv) Zinc min: about 2.9 mg;
  (v) Potassium min: about 2,450 mg;
  (vi) Magnesium min: about 82 mg; and/or
  (vii) Manganese min: about 2.45 mg In one or more preferred embodiments of the method of the present invention, the following dry ingredients are added to about 1 to 3 gallons of water at room temperature, e.g., about 20 to 27 degrees Celsius or about 68 to 80 degrees Fahrenheit, mixed, e.g., stirred, and served to an equine, or to livestock (e.g., pigs, sheep, goats, cattle), or to another type of hooved animal:
 a) about 10 to 30 grams of alfalfa, e.g., alfalfa powder; and
 b) about 10 to 30 grams of cane sugar.

In one or more preferred embodiments of the method of the present invention, the following dry ingredients are added to about 1 to 3 gallons of water at room temperature, e.g., about 20 to 27 degrees Celsius or about 68 to 80 degrees Fahrenheit, mixed, e.g., stirred, and served to an equine, or to livestock (e.g., pigs, sheep, goats, cattle), or to another type of hooved animal:
 a) about 10 to 30 grams of alfalfa, e.g., alfalfa powder; and
 b) about 10 to 50 grams of cane sugar.

In one or more preferred embodiments of the method of making a beverage of the present invention, the following dry ingredients are added to about 1 to 3 gallons of water at room temperature, e.g., about 20 to 27 degrees Celsius or about 68 to 80 degrees Fahrenheit, stirred and served to an equine, or to livestock (e.g., pigs, sheep, goats, cattle), or to another type of hooved animal:
 a) about 10 to 30 grams of alfalfa, e.g., alfalfa powder;
 b) about 10 to 30 grams of cane sugar; and
 c) one or more electrolytes, e.g., as follows:
  (i) about 40 to 132 mg Calcium;
  (ii) about 5,000 to 9,850 mg salt;
  (iii) about 1.5 to 2.3 mg Copper;
  (iv) about 1.5 to 2.9 mg Zinc;

(v) about 1,000 to 2,450 mg Potassium;
(vi) about 40 to 200 mg Magnesium;
(vii) about 2.45 to 5.5 mg Manganese; and/or
(viii) another desired electrolyte.

In one or more preferred embodiments of the method of making a beverage of the present invention, the following dry ingredients are added to about 1 to 3 gallons of water at room temperature, e.g., about 20 to 27 degrees Celsius or about 68 to 80 degrees Fahrenheit, stirred and served to an equine, or to livestock (e.g., pigs, sheep, goats, cattle), or to another type of hooved animal:
  a) about 10 to 30 grams of alfalfa, e.g., alfalfa powder;
  b) about 10 to 50 grams of cane sugar; and
  c) one or more electrolytes, e.g., as follows:
    (i) about 40 to 132 mg Calcium;
    (ii) about 5,000 to 9,850 mg salt;
    (iii) about 1.5 to 2.3 mg Copper;
    (iv) about 1.5 to 2.9 mg Zinc;
    (v) about 1,000 to 2,450 mg Potassium;
    (vi) about 40 to 200 mg Magnesium;
    (vii) about 2.45 to 5.5 mg Manganese; and/or
    (viii) another desired electrolyte.

One or more preferred embodiments of a beverage of the present invention promotes equine hydration and encourages equines, and/or livestock (e.g., pigs, sheep, goats, cattle), and/or another type of hooved animal to drink the beverage that contains water.

One or more preferred embodiments of a beverage of the present invention can be provided to horses, and/or to other equines, and/or to livestock (e.g., pigs, sheep, goats, cattle), and/or another type of hooved animal that compete or participates in shows to provide quicker recovery of muscles through good hydration before, during, and after competitions.

One or more preferred embodiments of a beverage of the present invention is a horse and/or other equine, and/or livestock (e.g., pigs, sheep, goats, cattle), and/or another type of hooved animal post-workout beverage that provides faster turnaround and bounce back after hard workouts and lessons and competition prep.

One or more preferred embodiments of a beverage of the present invention is a horse and/or other equine, and/or livestock (e.g., pigs, sheep, goats, cattle), and/or another type of hooved animal hauling water that provides a solution for horses or other equines on the road that are picky drinkers to promote drinking during travelling. The beverage can be served before, during and after travel.

One or more preferred embodiments of a beverage of the present invention is a mare recovery water that promotes hydration for mares and/or other equine females after foaling and while lactating.

One or more preferred embodiments of a beverage of the present invention is a recovery water that promotes hydration for female livestock, and/or other female hooved animals after giving birth and while lactating.

One or more preferred embodiments of a beverage of the present invention is a post-surgery recovery water for horses and/or other equines, and/or livestock (e.g., pigs, sheep, goats, cattle), and/or another type of hooved animal, providing important hydration after surgeries.

One or more preferred embodiments of a beverage of the present invention is a heat stress fluid for horses and/or other equines, and/or livestock (e.g., pigs, sheep, goats, cattle), and/or another type of hooved animal, providing a great tasting treat to serve on a hot summer's day and can be served chilled.

One or more preferred embodiments of a beverage of the present invention is a medical and supplement water, providing an easy way to deliver medications and supplements to horses and/or other equines, and/or livestock (e.g., pigs, sheep, goats, cattle), and/or another type of hooved animal.

One or more preferred embodiments of a beverage of the present invention is a healthy digestive water promoting good hydration, which is beneficial in maintaining a healthy digestive track for horses and/or other equines, and/or livestock (e.g., pigs, sheep, goats, cattle), and/or another type of hooved animal.

One or more preferred embodiments of a beverage of the present invention is delicious to horses and/or other equines, and/or livestock (e.g., pigs, sheep, goats, cattle), and/or another type of hooved animal, generally take to it and drink it quickly.

One or more preferred embodiments of the present invention is a dry or powdered blend of ingredients including alfalfa, e.g., alfalfa powder or alfalfa meal, that can be added to a liquid, e.g., water, to form or make a beverage for horses and/or other equines, and/or livestock (e.g., pigs, sheep, goats, cattle), and/or another type of hooved animal.

In a preferred embodiment of a dry or powdered blend of ingredients of the present invention, the blend comprises:
  a) about 25 grams of alfalfa, e.g., alfalfa powder;
  b) about 25 grams of cane sugar; and
  c) electrolytes as follows:
    (i) Calcium min: about 82 mg; calcium max: about 132 mg;
    (ii) salt min: about 9,850 mg; salt max: about 10,650 mg;
    (iii) Copper min: about 2.3 mg;
    (iv) Zinc min: about 2.9 mg;
    (v) Potassium min: about 2,450 mg;
    (vi) Magnesium min: about 82 mg; and
    (vii) Manganese min: about 2.45 mg.

In another preferred embodiment of a dry or powdered blend of ingredients, the blend comprises:
  a) about 15 grams of alfalfa, e.g., alfalfa powder;
  b) about 50 grams of cane sugar; and
  c) electrolytes as follows:
    (i) Calcium min: about 82 mg; calcium max: about 132 mg;
    (ii) salt min: about 9,850 mg; salt max: about 10,650 mg;
    (iii) Copper min: about 2.3 mg;
    (iv) Zinc min: about 2.9 mg;
    (v) Potassium min: about 2,450 mg;
    (vi) Magnesium min: about 82 mg; and
    (vii) Manganese min: about 2.45 mg.

In one or more preferred embodiments of a dry or powdered blend of ingredients of the present invention, the blend comprises:
  a) about 10 to 30 grams of alfalfa, e.g., alfalfa powder;
  b) about 10 to 30 grams of sugar, e.g., cane sugar; and
  c) one or more electrolytes as follows:
    (i) about 40 to 132 mg Calcium;
    (ii) about 5,000 to 9,850 salt min;
    (iii) about 1.5 to 2.3 Copper min;
    (iv) about 1.5 to 2.9 Zinc;
    (v) about 1,000 to 2,450 Potassium;
    (vi) about 40 to 200 Magnesium;
    (vii) about 2.45 to 5.5 Manganese; and/or
    (viii) another desired electrolyte.

In one or more preferred embodiments of a dry or powdered blend of ingredients of the present invention, the blend comprises:
a) about 10 to 30 grams of alfalfa, e.g., alfalfa powder;
b) about 10 to 50 grams of sugar, e.g., cane sugar; and
c) one or more electrolytes as follows:
(i) about 40 to 132 mg Calcium;
(ii) about 5,000 to 11,000 salt min;
(iii) about 1.5 to 2.3 Copper min;
(iv) about 1.5 to 2.9 Zinc;
(v) about 1,000 to 2,450 Potassium;
(vi) about 40 to 200 Magnesium;
(vii) about 2.45 to 5.5 Manganese; and/or
(viii) another desired electrolyte.

In one or more preferred embodiments of a dry or powdered blend of ingredients of the present invention, the blend comprises:
a) about 10 to 50 grams of alfalfa, e.g., alfalfa powder;
b) about 10 to 50 grams of sugar, e.g., cane sugar; and
c) one or more electrolytes as follows:
(i) about 40 to 132 mg Calcium;
(ii) about 5,000 to 9,850 salt min;
(iii) about 1.5 to 2.3 Copper min;
(iv) about 1.5 to 2.9 Zinc;
(v) about 1,000 to 2,450 Potassium;
(vi) about 40 to 200 Magnesium;
(vii) about 2.45 to 5.5 Manganese; and/or
(viii) another desired electrolyte.

In one or more preferred embodiments of a dry or powdered blend of ingredients of the present invention, the blend comprises:
a) about 10 to 30 grams of alfalfa, e.g., alfalfa powder; and
b) about 10 to 30 grams of sugar, e.g., cane sugar.

In one or more preferred embodiments of a dry or powdered blend of ingredients of the present invention, the blend comprises:
a) about 10 to 30 grams of alfalfa, e.g., alfalfa powder; and
b) about 10 to 50 grams of sugar, e.g., cane sugar.

In one or more preferred embodiments, a dry or powdered blend of ingredients of the present invention, can be added to a liquid, e.g., preferably water, and stirred and then served to an equine, and/or to livestock (e.g., pigs, sheep, goats, cattle), and/or to another type of hooved animal.

In one or more preferred embodiments, a dry or powdered blend of ingredients of the present invention, can be added to a liquid, e.g., preferably water, and mixed and then served to an equine, and/or to livestock (e.g., pigs, sheep, goats, cattle), and/or to another type of hooved animal.

In one or more preferred embodiments, a dry or powdered blend of ingredients of the present invention, can be added to a liquid, e.g., preferably water, and stirred until mixed and then served to a horse, and/or to another type of equine, and/or to livestock (e.g., pigs, sheep, goats, cattle), and/or to another type of hooved animal.

In one or more preferred embodiments, a dry or powdered blend of ingredients of the present invention, can be added to a liquid, e.g., preferably water, and stirred until mixed, e.g., stirred, for about 0 to 60 seconds, or preferably for about 10 to 60 seconds, and then served to an equine, and/or to livestock (e.g., pigs, sheep, goats, cattle), and/or to another type of hooved animal.

In one or more preferred embodiments of a method of making a dry or powdered blend of ingredients of the present invention, the blend is made by: adding desired amounts of selected dry ingredients and mixing, e.g., stirring, shaking, or using mechanical agitation.

In one or more preferred embodiments of making a beverage of the present invention, the method includes combining a dry or powdered blend of the present invention with a fluid or liquid, e.g., water, and mixing. The fluid and dry or powdered blend can be mixed by stirring, mechanical agitation, or shaking, for example. After preparing the beverage, the beverage can be served to equines, e.g., horses, mules, zebras, ponies and/or donkeys, and/or to livestock (e.g., pigs, sheep, goats, cattle), and/or to another type of hooved animal.

In one preferred embodiment of the present invention, a beverage of the present invention comprises alfalfa, e.g., preferably alfalfa leaf powder or alfalfa meal added to a liquid, e.g., preferably water.

In one preferred embodiment of the present invention, the beverage comprises alfalfa, e.g., preferably alfalfa leaf powder or alfalfa meal, and a sweetener, e.g., sugar, added to a liquid, e.g., water.

In one preferred embodiment of the present invention, the beverage comprises alfalfa, e.g., preferably alfalfa leaf powder or alfalfa meal, a sweetener, e.g., preferably sugar, and optionally one or more desired electrolytes added to a liquid, e.g., preferably water.

In one preferred embodiment of the present invention, the beverage comprises alfalfa, e.g., preferably alfalfa leaf powder or alfalfa meal, a sweetener, e.g., preferably sugar, and one or more desired electrolytes added to a liquid, e.g., preferably water.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired flavoring.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired flavoring; and
2) electrolytes.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired flavoring;
2) electrolytes; and
3) sweetener.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired flavoring; and
2) sweetener, e.g., sugar.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring; and
2) electrolytes.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring;
2) electrolytes; and
3) sweetener.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring; and
2) sweetener, e.g., sugar.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired flavoring;
2) sugar; and
3) electrolytes.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring;
2) sugar; and
3) electrolytes.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired flavoring, e.g., one or more of the following: alfalfa, peppermint, apple, mint, alfalfa mint.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired flavoring, e.g., one or more of the following: alfalfa, peppermint, apple, mint, alfalfa mint; and
2) a sweetener, e.g., sugar.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired flavoring, including one or more of the following: alfalfa, peppermint, apple, mint, alfalfa mint; and
2) electrolytes.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired flavoring, including one or more of the following: alfalfa, peppermint, apple, mint, alfalfa mint;
2) sweetener; and
3) electrolytes.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring, including one or more of the following: alfalfa, peppermint, apple, mint, alfalfa mint.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring, including one or more of the following: alfalfa, peppermint, apple, mint, alfalfa mint;
2) sugar; and
3) electrolytes.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring, including one or more of the following: alfalfa, peppermint, apple, mint, alfalfa mint;
2) sugar; and
3) electrolytes.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring, including one or more of the following: alfalfa, peppermint, apple, mint, alfalfa mint; and
2) sweetener.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink water and promote hydration includes:
1) desired dry or powdered flavoring, including one or more of the following: alfalfa, peppermint, apple, mint, alfalfa mint; and
2) sugar.

In another preferred embodiment of the present invention, a supplement for adding to a liquid, e.g., preferably water, to encourage equines, and/or to encourage livestock (e.g., pigs, sheep, goats, cattle), and/or to encourage another type of hooved animal to drink and promote hydration includes:
1) desired dry or powdered flavoring, including one or more of the following: alfalfa, peppermint, apple, mint, alfalfa mint; and
2) electrolytes.

In a preferred embodiment, a supplement for adding to a liquid to encourage equines, and/or to encourage livestock (e.g., pigs, sheep, goats, cattle), and/or to encourage another type of hooved animal to drink and promote hydration includes:
one or more types of desired dry or powdered or liquid flavoring, that preferably will encourage or entice a said animal to drink.

In a preferred embodiment, a supplement for adding to a liquid to encourage equines, and/or to encourage livestock (e.g., pigs, sheep, goats, cattle), and/or to encourage another type of hooved animal to drink and promote hydration includes:
one or more types of desired dry or powdered or liquid flavoring that are water
soluble, that preferably will encourage or entice a said animal to drink.

In or more preferred embodiments, a flavoring added to a liquid can be a sweetener.

In a preferred embodiment, a supplement for adding to a liquid to encourage equines, and/or to encourage livestock (e.g., pigs, sheep, goats, cattle), and/or to encourage another type of hooved animal to drink and promote hydration includes:
1) one or more types of desired dry or powdered or liquid flavoring; and
2) a desired sweetener.

In a preferred embodiment, a supplement for adding to a liquid to encourage equines, and/or to encourage livestock (e.g., pigs, sheep, goats, cattle), and/or to encourage another type of hooved animal to drink and promote hydration includes:
1) one or more types of desired dry or powdered or liquid flavoring; and
2) a desired sweetener; and/or
3) an electrolyte, if desired.

In a preferred embodiment, a supplement for adding to a liquid to encourage equines, and/or to encourage livestock (e.g., pigs, sheep, goats, cattle), and/or to encourage another type of hooved animal to drink and promote hydration includes:
1) one or more types of desired dry or powdered or liquid flavoring; and
2) a desired sweetener; and/or
3) one or more different types of electrolytes, if desired.

In a preferred embodiment, a supplement for adding to a liquid to form a beverage for an equine, hooved animal or livestock comprises:
a) 10 to 30 grams of desired flavoring;
b) 10 to 50 grams of sweetener; and/or
c) one or more electrolytes as follows:
(i) 40 to 400 milligrams of calcium
(ii) 4,000 to 11,000 milligrams of salt;
(iii) 1.5 to 5 milligrams of copper;
(iv) 1.5 to 6.5 milligrams of zinc;
(v) 1,000 to 5,000 milligrams of potassium;
(vi) 40 to 200 milligrams of magnesium; and/or
(vii) 2 to 6 milligrams of manganese.

In a preferred embodiment, a supplement for adding to a liquid to form a beverage for an equine, hooved animal or livestock comprises:
a) desired flavoring;
b) desired sweetener; and/or
c) one or more electrolytes as follows:
(i) 40 to 400 milligrams of calcium
(ii) 4,000 to 11,000 milligrams of salt;
(iii) 1.5 to 5 milligrams of copper;
(iv) 1.5 to 6.5 milligrams of zinc;
(v) 1,000 to 5,000 milligrams of potassium;
(vi) 40 to 200 milligrams of magnesium; and/or
(vii) 2 to 6 milligrams of manganese.

In one or more preferred embodiments of a supplement, or a dry or powdered blend, or a beverage of the present invention, alfalfa leaf powder can be substituted with alfalfa meal or another dry alfalfa product that can be mixed in a liquid, e.g., water.

In one or more preferred embodiments of a supplement, or a beverage of the present invention, alfalfa leaf powder can be substituted with alfalfa flavoring, e.g., in liquid form, and which preferably is a natural alfalfa flavoring.

In one or more preferred embodiments of a supplement, or a beverage of the present invention, flavoring can be alfalfa, peppermint, apple, mint, alfalfa mint, or another desired flavoring in liquid form.

In one or more preferred embodiments of a supplement, or a beverage of the present invention, any desired sweetener that is not harmful to, and which tastes good to an animal that is being offered the beverage can be included.

In one or more preferred embodiments of a supplement, or a beverage of the present invention, flavoring can be a combination of dry and liquid flavoring, if desired.

In one or more preferred embodiments, iron can also be added to a beverage of the present invention if desired.

When experimenting with alfalfa to use in the present invention, finding an alfalfa that provided the desired benefits, color and that was water soluble was challenging. The process used to dehydrate alfalfa and the grade of alfalfa used in the mix was found to be important to get the desired health benefits in the beverage and to also have the dry ingredients easily dissolve and/or mix in water.

In a most preferred embodiment, the process of making the alfalfa added to the dry mix of ingredients is important. In a most preferred embodiment of the present invention that includes alfalfa as part of a dry mix of ingredients, only the leaves and very few stems are used in processing the alfalfa. The alfalfa is graded and only the brightest green color of alfalfa is preferably used, instead of the brown or yellow potions of alfalfa. The alfalfa is preferably first sun dried and then kiln dried to obtain a most dehydrated version. The process then involves removing the seeds and large stems and only the smallest of stems and the leaves go through to the next stage. The dehydrated leaves and stems of alfalfa that are chosen to be included are then put into a vat where the alfalfa is further refined, most preferably through a #80 screen mesh to obtain the finest powder. This enables the powder to be water soluble and to mix instantly or about instantly with water. Other grade screens, e.g., 60 to 90 mesh screens, can also be used, with a preference to further refine the alfalfa to be water soluble. Through experimentation #80 mesh has been found to be most preferable. The refined alfalfa is then ready to be added to water or desired liquid alone or with other desired ingredients. In a most preferred embodiment, after refining the alfalfa through a mesh screen, then the remaining desired dry ingredients can be added, e.g., sweetener and/or desired electrolytes are simply added to the dehydrated and refined alfalfa. The dry mix is then ready to be added to water to form a beverage of the present invention. Alfalfa processed as described above can be obtained from BevSource™ via custom order.

In one or more preferred embodiments, alfalfa refined with at least a #60 screen mesh is included.

In one or more preferred embodiments, alfalfa refined with at least a #80 screen mesh is included.

In one or more preferred embodiments, human grade alfalfa is used as part of a dry mix and is soluble in water for offering to equines, livestock and/or other hooved animals.

In one or more preferred embodiments, a fine mesh (#80) is used to grind alfalfa leaves into a fine water soluble powder.

In one or more preferred embodiments, the alfalfa powder retains a vibrant green for the human eye.

In one or more other preferred embodiments, alfalfa in liquid or tea form can also be added to water or a desired liquid to form a beverage to serve to equines, livestock or other hooved animals. A dry powdered form of alfalfa that is water soluble is however most preferred because this has a longer shelf life and is easier to package and ship in dry form.

In one or more preferred embodiments of the present invention the following ingredients are added to about 2 gallons of water to form a beverage to serve to an equine, livestock or other hooved animal:
a) about 25 grams—alfalfa powder;
b) about 50 grams—cane sugar; and
c) about 15 grams—desired electrolytes.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 1 is a nutritional analysis panel for a preferred embodiment of a dry or powdered blend of ingredients of the present invention for adding to a liquid, e.g., water to make a preferred embodiment of a beverage of the present invention;

FIG. 2 is a nutritional analysis panel for another preferred embodiment of a dry or powdered blend of ingredients of the present invention for adding to a liquid, e.g., water to make a beverage of the present invention;

FIG. 3 is a nutritional analysis panel for another preferred embodiment of a dry or powdered blend of ingredients of the present invention for adding to liquid, e.g., water to make a beverage of the present invention; and FIG. 4 is a nutritional analysis panel for another preferred embodiment of a dry or powdered blend of ingredients of the present invention for adding to liquid, e.g., water to make a beverage of the present invention.

DETAILED DESCRIPTION OF THE INVENTION

FIGS. 1-3 are nutritional analysis panels for preferred embodiments of a dry or powdered blend of ingredients of the present invention for adding to a liquid, e.g., water, to make a preferred embodiment of a beverage of the present invention. FIG. 4 is a nutritional panel for an electrolyte blend or mix that can be included in a dry or powdered blend of ingredients, for example.

In a preferred embodiment of the present invention, a dry or powdered blend of ingredients of the present invention is provided for adding to a liquid, e.g., water, to form a beverage that can be provided to equines, and/or to livestock (e.g., pigs, sheep, goats, cattle), and/or to another type of hooved animal. The blend comprises: sugar (e.g., cane sugar), and a blend of Alfalfa Leaf Powder, Sodium Chloride, Potassium Chloride, Calcium Citrate, Magnesium Citrate, Zinc Gluconate, Copper Gluconate, Manganese Citrate), Maltodextrin.

In another preferred embodiment of the present invention, a dry or powdered blend of ingredients of the present invention is provided for adding to a liquid, e.g., water to form or make a beverage that can be provided to equines, and/or to livestock (e.g., pigs, sheep, goats, cattle), and/or to another type of hooved animal. The blend comprises: sugar (e.g., cane sugar), alfalfa, sodium chloride, potassium chloride, maltodextrin, calcium citrate, magnesium citrate, zinc gluconate, copper gluconate, and manganese citrate.

In one or more preferred embodiments, to make a beverage of the present invention, a bucket or container can be filled with liquid, e.g., water, e.g., 2 gallons of the liquid or 1 to 4 gallons of the liquid. A dry or powdered blend of the present invention, or other desired flavoring, can be added to the liquid. Stir until mixed to complete making the beverage and serve.

In one or more preferred embodiments an alfalfa leaf powder used is 100% alfalfa leaf powder. Alfalfa meal can also be used.

In one or more preferred embodiments, a beverage of the present invention can be served to equines, e.g., horses, mules, zebras and/or donkeys.

In one or more preferred embodiments, a beverage of the present invention can be served to livestock, e.g., pigs, sheep, goats, cattle.

In one or more preferred embodiments, a beverage of the present invention can be served to a hooved animal.

In one or more preferred embodiments, a beverage of the present invention can be served to equines, and/or to livestock (e.g., pigs, sheep, goats, cattle), and/or to another type of hooved animal, as needed for rehydration, after workouts, during travel, to aid dispensing medications or as a treat.

In one or more preferred embodiments, a beverage of the present invention can be provided as a sport beverage to equines, and/or to livestock, and/or to another type of hooved animal that competes or participates in shows.

FIG. 1 illustrates a nutritional analysis breakdown for a 94 gram serving of a dry or powdered mix in a preferred embodiment of the present invention. The composition of a preferred embodiment of a dry or powdered blend of ingredients in the nutritional analysis as shown in FIG. 1 can comprise the following:
a) 15 grams of Alfalfa powder;
b) 49.9 grams of cane sugar; and
c) electrolytes as follows:
  (i) 132 mg Calcium;
  (ii) 4125 mg salt;
  (iii) 9 mg iron;
  (iv) 2450 mg potassium;
  (v) 82 mg magnesium;
  (vi) 2.9 mg zinc;
  (vii) 2.3 mg copper; and
  (viii) 2.45 mg manganese.

FIG. 2 illustrates a nutritional analysis breakdown for a 94 gram serving of a dry or powdered mix in another preferred embodiment of the present invention. The composition of a preferred embodiment of a dry or powdered blend of ingredients in the nutritional analysis as shown in FIG. 2 can comprise the following:
a) 15 grams of Alfalfa powder;
b) 49.9 grams of cane sugar; and
c) 29.1 grams of electrolytes including the following:
  (i) 132 mg Calcium;
  (ii) 10,250 mg salt;
  (iii) 2.3 mg copper;
  (iv) 82.00 mg magnesium;
  (v) 2.45 mg manganese;
  (vi) 2450 mg potassium; and
  (vii) 2.90 mg zinc.

FIG. 3 illustrates a nutritional analysis breakdown for an 84 gram serving of a preferred embodiment of a dry or powdered mix that can be added to a liquid to form a beverage of the present invention. This can include the same mix of ingredients as set forth in FIG. 2, with being packaged as a smaller serving size.

FIG. 4 illustrates a nutritional analysis breakdown for 100 grams of a dry or powdered electrolyte mix in a preferred embodiment of the present invention. A desired amount of an electrolyte mix can be added to a dry blend of ingredients including alfalfa powder by itself, or including alfalfa powder and a sweetener, e.g., cane sugar. For example, in a preferred embodiment, a dry or powdered blend of ingredients of the present invention that can be added to a liquid to form a beverage comprises:
  a) electrolyte mix of FIG. 4—22.62%;
  b) sugar—59.52%; and
  c) alfalfa leaf powder—17.86%.

In another preferred embodiment, a dry or powdered mix of the present invention comprises:
  a) electrolyte mix—about 22 to 23%;
  b) sugar—about 59 to 60%; and
  c) alfalfa leaf powder about 17 to 18%.

In another preferred embodiment, a dry or powdered mix of the present invention comprises:
  a) electrolyte mix—about 22 to 23% (plus or minus 5 percent);
  b) sweetener—about 59 to 60% (plus or minus 5 percent); and
  c) desired flavoring—about 17 to 18% (plus or minus 5 percent).

In another preferred embodiment, a dry or powdered mix of the present invention comprises:
  a) electrolyte mix—about 22 to 23% (plus or minus 10 percent);
  b) sweetener—about 59 to 60% (plus or minus 10 percent); and
  c) desired flavoring—about 17 to 18% (plus or minus 10 percent).

In another preferred embodiment, a dry or powdered mix of the present invention for preferably adding to about 2 gallons of water comprises:
  a) about 15 to 25 grams— alfalfa powder;
  b) about 30 to 50 grams—cane sugar; and
  c) about 15 to 25 grams—desired electrolytes.

In another preferred embodiment, a dry or powdered mix of the present invention for preferably adding to about 2 gallons of water comprises:
  a) about 25 grams— alfalfa powder;
  b) about 50 grams—cane sugar; and
  c) about 15 grams—desired electrolytes.

In another preferred embodiment, a dry or powdered mix of the present invention for preferably adding to about 2 gallons of water comprises:
  a) about 10 to 30 grams— alfalfa powder;
  b) about 0 to 50 grams—cane sugar; and
  c) about 10 to 30 grams—desired electrolytes.

In another preferred embodiment, a dry or powdered mix of the present invention for preferably adding to about 1 to 4 gallons of water comprises:
  a) about 10 to 30 grams—alfalfa powder;
  b) about 0 to 25 grams—cane sugar; and
  about 10 to 30 grams—desired electrolytes In another preferred embodiment, a dry or powdered mix of the present invention for preferably adding to about 1 to 4 gallons of water comprises:
  a) a desired amount of alfalfa or other flavoring;
  b) about 0 to 50 grams—cane sugar; and/or
  c) a desired amount and types of desired electrolytes.

In another preferred embodiment, a dry or powdered mix of the present invention for preferably adding to about 1 to 4 gallons of water comprises:
  a) a desired amount of alfalfa or other flavoring, e.g., 0 to 25 grams;
  b) about 0 to 50 grams—sweetener or cane sugar; and/or
  c) a desired amount and types of desired electrolytes, e.g., 0 to 25 grams.

In another preferred embodiment, a dry blend of ingredients can include an electrolyte mix that is 15 to 85% of the dry blend (plus or minus 5%), a sweetener that is 0 to 60% (plus or minus 5%) of the dry blend and the alfalfa leaf powder that is 15 to 85% (plus or minus 5%) of the dry blend.

The composition of another preferred embodiment of a dry or powdered blend of ingredients in the nutritional analysis as shown in FIG. 2 can comprise the following:
  a) 15 grams of Alfalfa powder;
  b) 49.9 grams of cane sugar; and
  c) electrolytes including the following:
    (i) 132 mg Calcium;
    (ii) 10,250 mg salt;
    (iii) 2.3 mg copper;
    (iv) 82.00 mg magnesium;
    (v) 2.45 mg manganese;
    (vi) 2450 mg potassium; and
    (vii) 2.90 mg zinc.

A dry or powdered blend of ingredients of the present invention can be added to preferably about 1 to 4 gallons of water and mixed, e.g., stirred, to form a beverage of the present invention. The beverage then can be served to a horse or other equine, or to livestock (e.g., pigs, sheep, goats, cattle), or to another type of hooved animal. The beverage can be served immediately after mixing. The beverage can also be served to a horse or other equine, or to livestock (e.g., pigs, sheep, goats, cattle), or to another type of hooved animal, within 24 to 48 hours after mixing.

In preferred embodiments, a shelf life of the dry or powdered blend is preferably at least 18 months.

In preferred embodiments, a shelf life of a beverage of the present invention is at least 24 to 48 hours.

In one or more preferred embodiments a dry or powder blend of ingredients of the present invention can be sugar free with desired flavoring and/or electrolytes.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the claims.

The invention claimed is:
1. A method for promoting hydration of an equine, livestock, or a hooved animal, or for encouraging the equine, livestock or hooved animal to drink, comprising the following steps:
  a) providing a beverage or liquid to the equine, livestock or hooved animal, the beverage or liquid comprising:
    i) a sweetener;
    ii) a hydration blend including alfalfa powder and optionally another desired flavoring, and optionally one or more desired electrolytes; and
    iii) water; and
  b) allowing the equine, livestock, or hooved animal to drink the beverage or liquid.

2. The method of claim 1 wherein the beverage or liquid in step "a" is provided after competition for helping the equine's, livestock's or hooved animal's muscles recover after competition.

3. The method of claim 1 wherein the beverage or liquid in step "a" is provided during travel for enticing the equine, hooved animal or livestock to drink the beverage or fluid while travelling.

4. The method of claim 1 wherein the beverage or liquid is provided in step "a" after hard workouts, lessons or competition preparation to enable faster turnaround and bounce back of the equine, hooved animal or livestock.

5. The method of claim 1 wherein the beverage or liquid is provided in step "a" to a mare or female livestock or a female hooved animal after foaling or giving birth or while lactating for helping recovery of the mare or female hooved animal or female livestock after foaling or giving birth or while lactating.

6. The method of claim 1 wherein the beverage or liquid is provided in step "a" after surgery for helping the equine, hooved animal or livestock recover after surgery.

7. The method of claim 1 wherein the beverage or liquid is also provided for treating heat stress of the equine, hooved animal or livestock, and further comprising a step of
chilling the beverage or liquid to 60 to 70 degrees Fahrenheit prior to step "a".

8. The method of claim 1 wherein the beverage or liquid is also provided to facilitate providing supplements or medicine to the equine, hooved animal or livestock and further comprising a step of
adding a desired supplement or medicine to the beverage or liquid prior to step "a".

9. The method of claim 1 wherein the beverage or liquid in step "a" is also provided for helping the equine, hooved animal or livestock maintain a healthy digestive track.

10. The method of claim 1 wherein the water of the beverage or liquid in step "a" weighs between 20 and 80 times a weight of the hydration blend.

11. A method for promoting hydration of an equine, livestock, or a hooved animal, or for enticing the equine livestock or hooved animal to drink, comprising the following steps:
a) adding a dry blend of ingredients to a liquid to form a beverage for the equine, livestock, or hooved animal, the dry blend of ingredients comprising
i) 10 to 30 grams of alfalfa powder that is human grade, refined using a mesh screen having a grade selected from a range of 60 to 90, and water soluble; and
ii) an electrolyte mix; and
b) allowing the equine, livestock or hooved animal to drink the beverage.

12. The method of claim 11 wherein the electrolyte mix in the dry blend of ingredients in step "a" comprises 10 to 20 grams of electrolytes.

13. The method of claim 12 wherein the dry blend of ingredients in step "a" further comprises 10 to 50 grams of a sweetener that is sugar.

14. The method of claim 12 wherein the electrolyte mix includes the following:
(i) 40 to 400 milligrams of calcium;
(ii) 4,000 to 11,000 milligrams of salt;
(iii) 1.5 to 5 milligrams of copper;
(iv) 1.5 to 6.5 milligrams of zinc;
(v) 1,000 to 5,000 milligrams of potassium;
(vi) 40 to 200 milligrams of magnesium; and
(vii) 2 to 6 milligrams of manganese.

15. The method of claim 11 wherein the alfalfa powder is refined using 80 grade mesh to enable the alfalfa powder to instantly, or at least almost instantly, dissolve in water.

16. The method of claim 11 wherein only alfalfa leaves are used to form the alfalfa powder of step "a".

17. The method of claim 11 wherein the alfalfa powder of step "a" comprises a majority percentage of alfalfa leaves and some alfalfa stems.

18. The method of claim 11 wherein only green parts of an alfalfa plant are used to make the alfalfa powder of step "a".

19. The method of claim 11 wherein the alfalfa powder of step "a" retains a green color after undergoing refining.

20. A method for promoting hydration of an equine, livestock, or a hooved animal, or for enticing the equine, livestock or hooved animal to drink, comprising the following steps:
a) adding a dry blend of ingredients to a liquid to form a beverage for the equine, livestock, or hooved animal, the dry blend of ingredients comprising:
i) an electrolyte mix;
ii) a sweetener; and
iii) an alfalfa powder that is adapted to instantly, or at least almost instantly, dissolve in water.

21. The method of claim 20 wherein the electrolyte mix is 22 to 23% of the dry blend (plus or minus 5%), the sweetener is 59 to 60% (plus or minus 5%) of the dry blend and the alfalfa powder is 17 to 18% (plus or minus 5%) of the dry blend.

22. The method of claim 1 wherein the another desired flavoring in the beverage or liquid of step "a" is selected from a group consisting of peppermint, apple, mint, and alfalfa mint.

* * * * *